United States Patent [19]

Duluco et al.

[11] Patent Number: 5,584,847
[45] Date of Patent: Dec. 17, 1996

[54] TROCAR FOR INSERTING ENDOSCOPY INSTRUMENTS INTO CAVITIES

[75] Inventors: Jean L. Duluco, Carignan; Jean Cuilleron, 57 Rue Francisque Voytier, 42100 Saint Etienne, both of France

[73] Assignee: Jean Cuilleron, France

[21] Appl. No.: 306,754

[22] Filed: Sep. 15, 1994

[30] Foreign Application Priority Data

Sep. 15, 1993 [FR] France .................................. 93 11359

[51] Int. Cl.⁶ .................................................. A61B 17/34
[52] U.S. Cl. ........................... 606/185; 604/164; 604/264
[58] Field of Search ................................ 604/164, 167, 604/264, 169; 606/185

[56] References Cited

U.S. PATENT DOCUMENTS

| | | | |
|---|---|---|---|
| 4,112,932 | 9/1978 | Chiulli | 128/3 |
| 5,053,016 | 10/1991 | Lander | 604/169 |
| 5,066,288 | 11/1991 | Deniega et al. | 604/274 |
| 5,104,383 | 4/1992 | Shichman | 604/167 |
| 5,112,321 | 5/1992 | Hiltebrandt | 604/264 |
| 5,211,633 | 5/1993 | Stouder, Jr. | 604/167 |
| 5,234,455 | 8/1993 | Mulhollan | 606/191 |
| 5,338,307 | 8/1994 | Stephens et al. | 604/167 |
| 5,380,288 | 1/1995 | Hart et al. | 604/167 |

FOREIGN PATENT DOCUMENTS 9214414  9/1992  WIPO .

*Primary Examiner*—Michael Powell Buiz
*Assistant Examiner*—Patrick W. Rasche
*Attorney, Agent, or Firm*—Eckert Seamans Cherin & Mellott

[57] ABSTRACT

Trocar for inserting endoscopy instruments into cavities, the trocar having a cleanable hollow body, a disposable tip which is equipped with a swivel valve that can be retracted by inserting the instrument through an internal channel in the tip that communicates with the hollow body. The disposable tip is also equipped with externally operable features capable of modifying the diameter of channel in order to match it to the diameter of the instrument to be inserted.

10 Claims, 2 Drawing Sheets

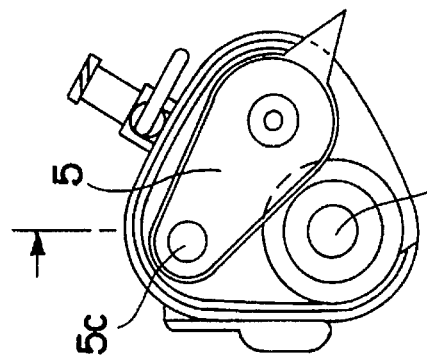
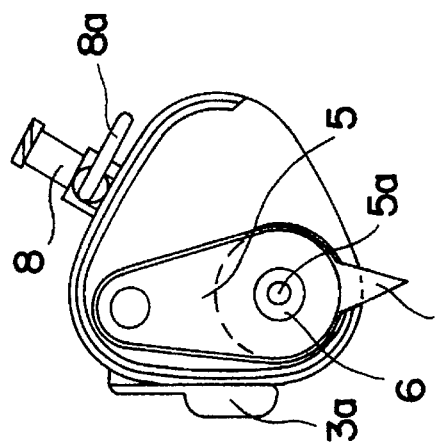
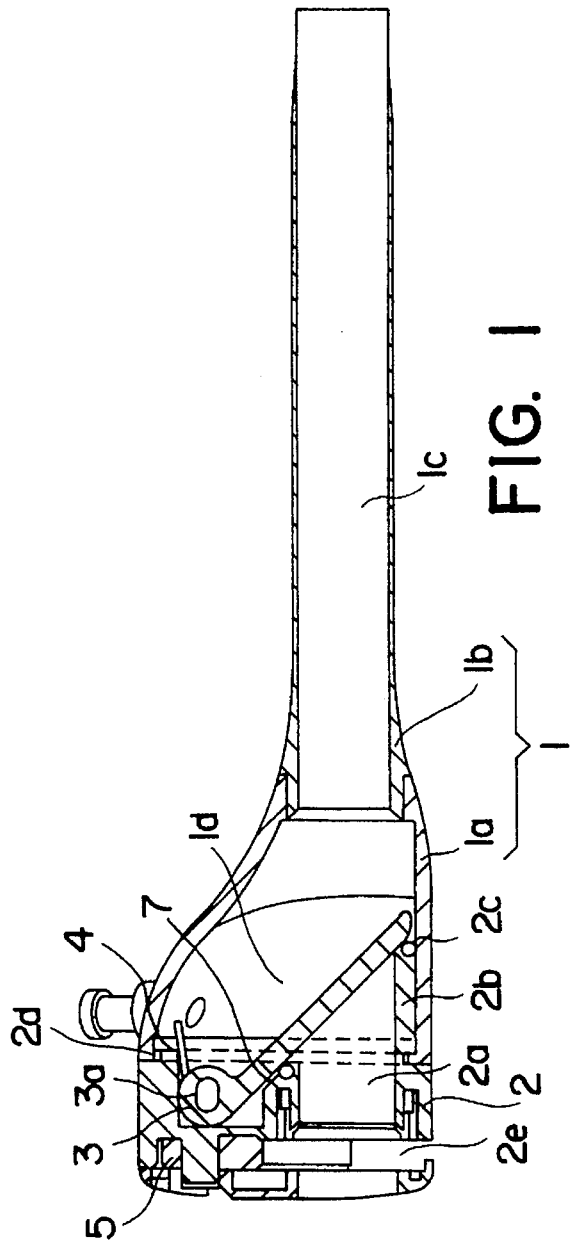
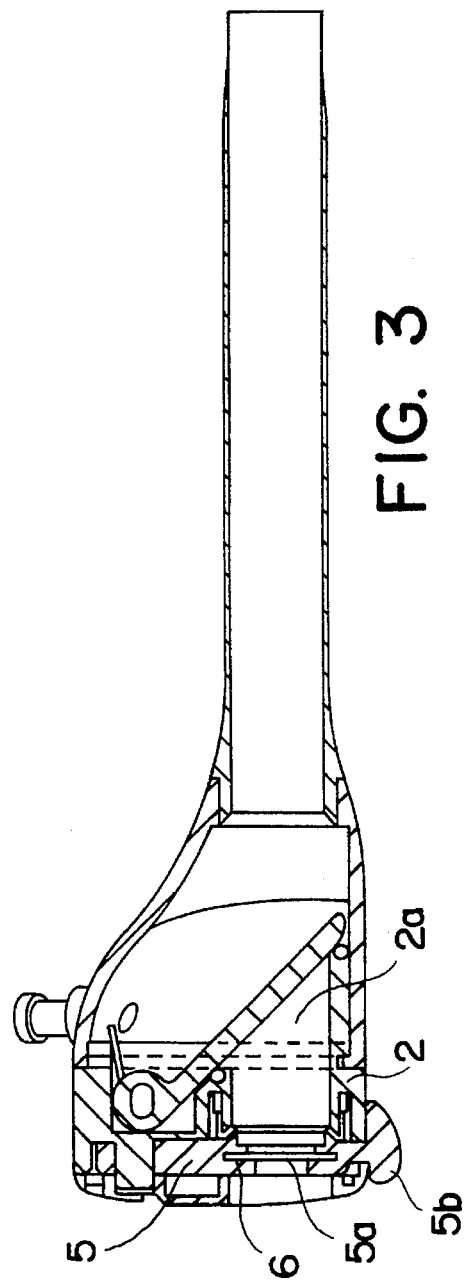

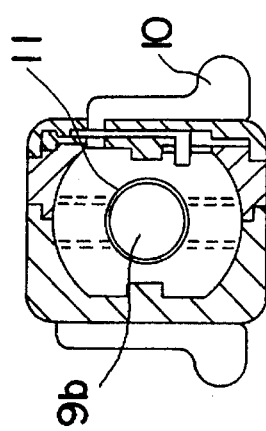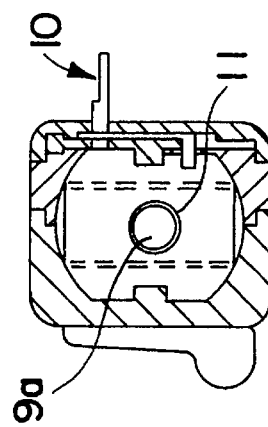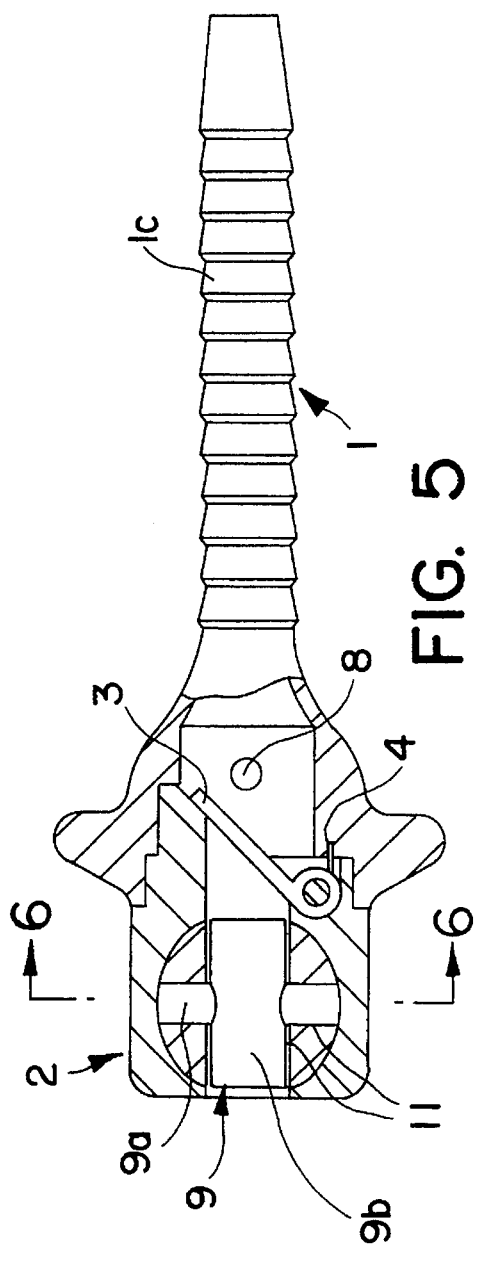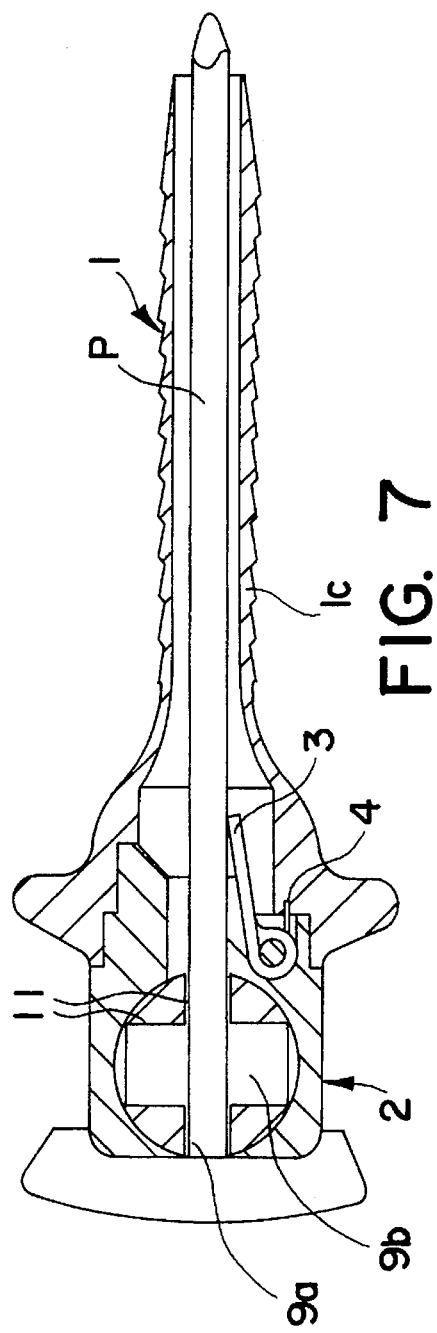

TROCAR FOR INSERTING ENDOSCOPY INSTRUMENTS INTO CAVITIES

BACKGROUND OF THE INVENTION

1. Field of the Invention

The invention relates to the technical field of surgical instruments.

2. Description of the Prior Art

In some surgical interventions, the use of trocars is known in order to allow the insertion of various types of endoscopy instruments, in particular into cavities in the human body. This applies, for instance, to pneumoperitonium where it is necessary to inflate the abdomen in order to allow the passage of instruments. The trocar is shaped in order to permit the injection of $CO_2$ in order to decompress the internal organs.

As is completely familiar to those skilled in the art, a trocar essentially comprises a hollow body of which the end has a tip fitted with an internal channel to allow the insertion of the instrument in question. This internal channel communicates with the hollow body. In order to ensure leaktightness when the instrument is withdrawn in order to prevent any loss of previously injected $CO_2$, the trocar has internal features capable of fulfilling this function.

Regardless of the ways in which trocars are designed, they are generally shaped to only allow the insertion of instruments having a clearly defined diameter. If it is necessary to change instruments during an operation and if the diameter of the instrument is greater or less than that of the trocar the surgeon is often confronted with real problems.

In order to attempt to overcome these drawbacks, trocars fitted with interchangeabe tips slide valves or swiveling discs have been proposed in order to match the various diameters of surgical instruments likely to be used. One might mention, for example, the teachings of patent WO-A-92444.

However, these solutions are unsatisfactory because they require the surgeon to carry out relatively awkward manipulations involving the use of both hands. In addition, these trocars do not always meet the requirement for leaktightness and are often very bulky. Finally, they are either disposable or resterilizable and necessitate complex disassembly and cleaning procedures.

SUMMARY OF THE INVENTION

The object of the invention is to overcome these drawbacks in a simple, safe, effective and rational manner.

The problems that the invention intends to solve are as follows:

Make it possible to modify the diameter of the inlet channel of the trocar tip, in order to adapt it to the diameter of the desired instrument in a compact, ergonomic apparatus with a reducing adapter and a valve seal built into the tip that can be operated externally using one hand with the other hand being able to continue holding the apparatus normally.

Make it possible to extract delicate or larger "objects" (needles, stones, etc.) during an intervention through the same trocar.

Make it possible to easily disassemble the tip of the trocar, the part that includes all the seals and mechanisms that are difficult to clean.

In order to solve such problems a semi-disposable two-piece trocar has been devised and developed of a type having a first cleanable, resterilizable part in the form of a hollow body and a second part formed by a tip equipped with means of sealing in the form of a shutter with a 45° valve mounted so that it swivels and accommodated in the tip of the trocar.

The tip is designed using a disposable material, if required, and includes all the seals and mechanisms that are difficult to clean. The two parts of the trocar are assembled by clicking them together or by any other process suitable for such a design. The tip is equipped with features that are completely enclosed, can be operated externally and capable of modifying, at any time during an intervention, the diameter of the channel in order to match it to the diameter of the instrument to be inserted by simply exerting finger pressure.

In order to solve the problem of adapting the trocar to the diameter of the instrument to be used, the internal features consist of reducing adapter actuated by a lever in order to coaxially align holes of different diameters with part of the channel into which the instrument is inserted.

In a first embodiment, the reducing adapter consists of a hinged arm having at least one hole of diameter smaller than that of the channel and capable of being coaxially aligned with said channel under the action of the lever.

In order to solve the problem of ensuring leaktightness after inserting the instrument in order to prevent any leak of $CO_2$, the arm is accommodated transversely in a housing formed in the thickness of the tip upstream from a seal of the inlet of the channel in the tip through which the instrument is inserted. The hole or holes of the arm have a sealing device that cooperates with the body of the corresponding instrument.

In another embodiment, the reducing adapter consists of a spherical plug having at least two through-holes of different diameter capable of being coaxially aligned with the channel under the action of the lever.

The two holes communicate with each other and are arranged in two orthogonal planes.

Each hole has a sealing device that cooperates with the body of the corresponding instrument Another problem that the invention aims to solve is to ensure self-penetration of the trocar and its retention in the opposite direction with a view to positioning the trocar correctly.

Such a problem is solved in that the body has, over all or part of its length, external annular peripheral ribs.

BRIEF DESCRIPTION OF THE DRAWING

The invention is explained below in more detail reference being made to the accompanying drawings in which:

FIG. 1 is a longitudinal sectional view of a first embodiment of the trocar.

FIG. 2 is a transverse sectional view along, line 2—2 in FIG. 1.

FIG. 3 is a view that corresponds to FIG. 1 showing how to change the diameter of the inlet channel.

FIG. 4 is a transverse sectional view along line 4—4 in FIG. 3.

FIG. 5 is a longitudinal sectional view of another embodiment of the trocar before an instrument is inserted.

FIG. 6 is a transverse sectional view along line 6—6 in FIG. 5.

FIG. 7 is a sectional view corresponding to FIG. 5 showing how to change the diameter of the inlet channel and the insertion of an instrument in the form of a punch.

FIG. 8 is a transverse sectional view along line 8—8 in FIG. 7.

DESCRIPTION OF THE PREFERRED EMBODIMENT

In order to make the following description more comprehensible, it is pointed out that the trocar comprises a body (1) equipped with a tip (2). The body comprises a tube (1b) underneath a bell-mouthed part (1a). Part (1b) is axially drilled at (1c) over its entire length whereas part (2) has an internal through-channel (2a). Hole (1c) and channel (2a) are in coaxial alignment. The surgical instrument that is to be used is inserted through internal channel (2a) in tip (2) so that it protrudes beyond the free end of body (1).

Bell-mouthed part (1a) has an internal recess (1d) that communicates with channel (2a) and hole (1c). This recess accommodates a swivel valve (3) of which the axis of rotation is situated in tip (2) and which is held in the shut-off position by spring (4). In the position where channel (2a) and hole (1c) are shut off, valve (3) rests against its seat (2b) comprising a seal (2c). Valve (3) is retracted under the effect of inserting the instrument; it can also be operated externally by simply exerting finger pressure on operating handle (3a) if the operator needs to extract delicate "objects" from the organism during an intervention.

According to one basic characteristic of the invention, tip (2) is fitted with internal features that can be operated externally and are capable of modifying the diameter of channel (2a) in order to match it to the diameter of the instrument to be inserted. As will be shown in the rest of this description, these features are shaped in order to ensure leaktightness inside the trocar after the instrument is inserted.

In the embodiment shown in FIGS. 1 to 4, the features consist of a reducing adapter in the form of a hinged arm (5) actuated by lever (5b). This arm (5) has at least one hole (5a) of diameter less than that of channel (2a) in tip (2). The arm is hinged at (5c) so that it swivels angularly when force is exerted on lever (5b) in order to line up holes (5a) and (2a) (FIGS. 3 and 4).

Reducing adapter (5) is accommodated transversely a housing (2e) formed in the thickness of tip (2). Said housing (2e) is designed either to coaxially align hole (5a) with channel (2a) (FIG. 3) or to completely free channel (2a) (FIGS. 1 and 2), depending on the angular position of lever (5b). The axis of rotation (5c) of reducing adapter (5) is parallel to the axis of the trocar.

It is clear that, depending on the angular position of reducing adapter (5), it is possible to modify the diameter of the inlet of channel (2a) in order to match it to the diameter of the instrument to be used. In order to ensure leaktightness, a seal (7) is fitted in the inlet of insertion channel (2a) in tip (2) upstream from hinged arm (5) and downstream from valve (3). The effect of this seal (7) is to ensure leaktightness of the instrument whose diameter corresponds to that of channel (2a), i.e. in the retracted position of reducing adapter (5) (FIGS. 1 and 2).

In order to ensure leaktightness in the case of an instrument of smaller diameter, i.e. when arm (5) is swivelled so that it lines up its hole (5a) with hole (2a) (FIG. 3), said hole (5a) has an internal seal (6) capable of cooperating with the body of the corresponding instrument.

Note that disposable tip (2) is connected to body (1) by a click-on system comprising a seal (2d) that ensures complete leaktightness between the two parts of the trocar.

In addition, in order to make it possible to re-inflate or deflate the peritonium, the trocar is equipped with a slide valve (8) that is opened or closed by a quarter-turn cock (8a).

In another embodiment, the reducing adapter consists of a spherical plug (9) having at least two through-holes (9a) (9b). These holes are of different diameter and are capable of being axially aligned with channel (2a) under the action of angular swivelling of lever (10).

Advantageously, plug (9) has two through-holes arranged in two orthogonal planes. Hole (9a) is of smaller diameter than channel (2a) whereas the diameter of hole (9b) is equal to the diameter of said channel. As previously, in order to ensure leaktightness after inserting the instrument, each hole (9a) (9b) has an internal seal (11). It is therefore sufficient to orientate the plug by actuating lever (10) in order to coaxially align either hole (9a) (FIGS. 5 and 6) or hole (9b) (FIGS. 7 and 8) with channel (2a) depending on the diameter of the desired instrument.

According to another characteristic, body (1) of the trocar has external annular peripheral ribs (1c) over all or part of its length.

The advantages are apparent from the description with special emphasis being placed on the following points:
- the facility to easily disassemble the tip and body of the trocar with a view to obtaining a disposable tip,
- the production of a compact, ergonomic trocar that includes, in its tip, a reducing adapter and a sealing valve that can be operated externally with one hand without having to release the trocar,
- the facility to modify the diameter of the insertion channel in the tip depending on the diameter of the instrument to be used,
- the facility to extract delicate "objects" during an intervention by manually retracting the sealing valve by using an external lever,
- the effectiveness of the result thus obtained.

We claim:

1. Trocar for inserting endoscopy instruments into cavities in the form of a hollow body comprising:

a cleanable, resterilizable hollow body and a disposable tip having a thickness and being formed with a channel having a diameter, the disposable tip being separably couplable to the cleanable, resterilizable hollow body;

a swivel mounted 45° valve coupled to the disposable tip; and externally operated features coupled to the disposable tip which are completely enclosed in the thickness of the disposable tip, said externally operated features being operable by finger pressure to change the diameter of the channel in order to match the diameter of the instrument to be inserted; wherein the disposable tip includes all seals and mechanisms to be cleaned wherein the externally operated features comprise a swivelling reducing adapter actuated by a lever.

2. Trocar as claimed in claim 1 wherein swivelling is reducing adapter formed with at least one hole differing in diameter from the diameter of the channel, the swivelling reducing adapter being completely enclosed in the disposable tip wherein the lever is capable of coaxially aligning the at least one hole with the channel through which the instrument is inserted.

3. Trocar as claimed in claim 2 wherein the reducing adapter consists of a hinged arm formed with at least one hole of diameter less than that of the channel and capable of being coaxially aligned with said channel under the action of the lever.

4. Trocar as claimed in claim 3 wherein the channel has an inlet and the arm is accommodated transversely in a housing formed in the thickness of the disposable tip upstream from a sealing device in the inlet of the channel in the disposable tip through which the instrument is inserted.

5. Trocar as claimed in claim 3 wherein the at least one hole in the arm has a sealing device that cooperates with the body of the corresponding instrument.

6. Trocar as claimed in claim 2 wherein the swiveling reducing adapter consists of a spherical plug having at least two through-holes of different diameter capable of being coaxially aligned with the channel under the action of the lever.

7. Trocar as claimed in claim 6 wherein the at least two holes communicate with each other and are arranged in two orthogonal planes.

8. Trocar as claimed in claim 7 wherein each of the at least two holes have a sealing device that cooperates with the body of the corresponding instrument.

9. Trocar as claimed in claim 1 wherein the 45° valve can be operated externally using one hand and can retract itself in order to completely free the channel to allow the removal of delicate "objects" during an intervention without releasing the trocar.

10. Trocar as claimed in claim 1 wherein the cleanable, resterilizable body has external annular peripheral ribs over at least part of its length.

* * * * *

UNITED STATES PATENT AND TRADEMARK OFFICE
CERTIFICATE OF CORRECTION

PATENT NO. : 5,584,847
DATED : December 17, 1996
INVENTOR(S) : Jean L. Dulucq and Jean Cuilleron It is certified that error appears in the above-indentified patent and that said Letters Patent is hereby corrected as shown below:

On the title page, item [19] should read:
— Dulucq et al. —

On the title page, item [75];
named inventor should be Jean L. Dulucq.

Column 3, line 42, after the word "transversely" insert ––in––.

Column 4, Claim 1, line 53, after the word "cleaned" insert ––,––.

Column 4, Claim 2, line 56, after the word "wherein" insert ––the––.

Column 4, Claim 2, line 56, after the word "swivelling" delete "is".

Column 4, Claim 2, line 57, after the word "adapter" insert ––is––.

Signed and Sealed this

Twenty-third Day of September, 1997

Attest:

BRUCE LEHMAN

Attesting Officer

Commissioner of Patents and Trademarks